(12) United States Patent
Yehuda

(10) Patent No.: US 6,713,511 B1
(45) Date of Patent: Mar. 30, 2004

(54) FATTY ACID DERIVATIVES

(76) Inventor: Zvi Yehuda, 3 Jabotinsky Street, 52520 Ramat Gan (IL)

(*) Notice: Subject to any disclaimer, the term of this patent is extended or adjusted under 35 U.S.C. 154(b) by 0 days.

(21) Appl. No.: 10/049,058

(22) PCT Filed: Aug. 11, 1999

(86) PCT No.: PCT/IL99/00437

§ 371 (c)(1),
(2), (4) Date: Feb. 7, 2002

(87) PCT Pub. No.: WO00/09476

PCT Pub. Date: Feb. 24, 2000

(30) Foreign Application Priority Data

Aug. 11, 1998 (IL) .................................. 125731
Apr. 19, 1999 (IL) .................................. 129500

(51) Int. Cl.⁷ .............................................. A61K 31/24
(52) U.S. Cl. ........................ 514/535; 514/560; 554/35; 554/51; 554/223; 554/224; 554/229; 562/553; 562/556
(58) Field of Search ................. 554/223, 224, 554/229, 35, 51; 562/553, 556; 514/535, 560

(56) References Cited

U.S. PATENT DOCUMENTS

| | | |
|---|---|---|
| 3,995,059 A | 11/1976 | Fukumaru et al. |
| 4,497,827 A | 2/1985 | Nelson |
| 4,826,877 A | 5/1989 | Stewart et al. |
| 4,851,431 A | 7/1989 | Yehuda |
| 4,868,212 A | 9/1989 | Horrobin |
| 5,120,763 A | 6/1992 | Yehuda |
| 5,216,023 A | 6/1993 | Literati |
| 5,288,755 A | 2/1994 | Yehuda |
| 5,416,114 A | 5/1995 | Yehuda |
| 5,468,776 A | 11/1995 | Yehuda |
| 5,591,446 A | 1/1997 | Melnik et al. |
| 5,599,840 A | 2/1997 | Yehuda |

FOREIGN PATENT DOCUMENTS

| | | | |
|---|---|---|---|
| JP | 2-225411 | | 9/1990 |
| WO | WO 89/07938 | * | 9/1989 |
| WO | WO 98/21949 | | 5/1998 |

OTHER PUBLICATIONS

Patent Abstracts of Japan, vol. 012, No. 299 (C–520), Aug. 15, 1988 & JP 63 068550 A (Tsumura Juntendo Inc.), Mar. 28, 1988.

Ungerstedt et al, "Quantitative Recording of Rotational Behavior in Rats After 6–Hydroxy–Dopamine Lesions of the Nigrostriatal Dopamine System", Brain Research, 24 (1970) 485–493.

Inman et al, "Amidination", Methods in Enzymology, vol. 91, p. 564, Academic Press, 1983.

* cited by examiner

Primary Examiner—Deborah D. Carr
(74) Attorney, Agent, or Firm—Nixon & Vanderhye P.C.

(57) ABSTRACT

The invention relates to a novel acylate which is the reaction product of (a) a substance which is selected from the group consisting of naturally occuring alpha-aminocarboxylic acids, neurotransmitters other than such acids, and central or peripheral nervous system pharmacologically active compounds, and containing a functional group including an acylatable hydrogen atom, or a reactive derivative thereof; and (b) an essential fatty acid or a reactive derivative thereof; and including the pharmaceutically acceptable salts of such acylates possessing a basic and (or) acidic function; and to their functional derivatives. The acylates and their functional derivatives may be used for treatment of a disease or condition related to a neurotransmitter defector deficiency, or to another central or peripheral nervous system defect or deficiency, and in particular Parkinson's disease.

17 Claims, No Drawings

FATTY ACID DERIVATIVES

This application is the US national phase of international application PCT/IL99/00437 filed Aug. 11, 1999 which designated the U.S.

FIELD AND BACKGROUND OF THE INVENTION

The present invention relates to acylates for treatment of a disease or condition related to a neurotransmitter defect or deficiency, or to another central or peripheral. nervous system defect or deficiency.

As detailed, for example, in U.S. Pat. No. 4,826,877 (Stewart et al.) and U.S. Pat. No. 4,868,212 (Horrobin), the essential fatty acids consist of the n-3 series derived from and including α-linolenic acid and the n-6 series derived from and including linoleic acid; since neither α-linolenic acid nor linoleic acid are manufactured in the body, they must be provided by food. The n-3 series thus includes α-linolenic, Δ-6,9,12,15-octadecatetraenoic, Δ-8,11,14,17-eicosatetraenoic, Δ-5,8,11,14,17-eicosapentaenoic, Δ-7,10, 13,16,19-docosapentaenoic and Δ-4,7,10,13,16,19-docosahexaenoic acids, and the n-6 series thus includes linoleic, Δ-6,9,12-octadecatrienoic (γ-linolenic), Δ-8,11,14,-eicosatrienoic (dihomo-γ-linolenic), Δ-5,8,11,14-eicosatetraenoic (arachidonic), Δ-7,10,13,16-docosatetraenoic (adrenic) and Δ-4,7,10,13,16-docosapentaenoic acids. The term "essential fatty acids" in the present specification and claims means all twelve of the above-mentioned fatty acids.

In U.S. Pat. No. 4,826,877, there is described use of the essential fatty acids for the prevention or treatment of diabetic neuropathy and other long term complications of diabetes mellitus. In U.S. Pat. No. 4,868,212, such acids are used in treatment of atopic disorders, while in U.S. Pat. No. 5,591,446 (Melnik et al.), γ-linolenic and/or dihomo-γ-linolenic acids are used for atopy prophylaxis. In U.S. Pat. No. 4,497,827 (Nelson), arachidonic acid analogues are utilized as anti-inflammatory, antiallergenic and antibrochoconstriction agents. In U.S. Pat. No. 3,995,059 (Fukumaru), N-(α-alkyl) benzylamides of $C_{13}$–$C_{25}$ aliphatic carboxylic acids are used for lowering elevated levels of cholesterol in the blood.

In U.S. Pat. Nos. 5,599,840, 5,468,776, 5,416,114, 5,288, 755, 5,120,763 and 4,851,431, to Yehuda, S., there are described compositions which comprise a combination of α-linolenic acid and linoleic acid, within a range of strictly defined proportions, stated to be useful in enhancing memory, producing analgesia, regulating sleep, inhibiting senility symptoms, and in treating Alzheimer's disease and related dementia, and epilepsy. In International Patent Application No. PCT/IL97/00366, published May 28, 1998 as WO 98/21949, the same inventor described the application of essentially the same combination of acids, for the treatment of multiple sclerosis. By contrast, use of mixtures of α-linolenic acid and linoleic acid in proportions outside of the specified range, or (as is implicit from the U.S. patents and explicit in WO 98/21949), each acid or γ-linolenic acid taken separately, or substituting γ-linolenic acid for α-linolenic acid in a pharmacologically active mixture with linoleic acid, did not afford any significant pharmacological activity.

The contents of the U.S. Patents referred to in the present application, and of WO 98/21949, are incorporated herein by reference.

To the best of the present inventor's knowledge, it has been neither disclosed nor suggested in the prior art, to utilize acylates derived from essential fatty acids, for treatment of a disease or condition related to a neurotransmitter defect or deficiency, or to another central or peripheral nervous system defect or deficiency. From another aspect, it does not appear to have been previously disclosed or suggested in the prior art, that essential fatty acids, by forming covalent bonds with naturally occurring α-aminocarboxylic acids, neurotransmitters other than such acids, or central or peripheral nervous system pharmacologically active compounds, would thereby have the ability to transport such substances, in the form of the resultant acylates, across the blood-brain barrier.

Although a vast number of drugs are known to medicine, many do not realize their full potential because of the problem of applying them at an internal body site (such as appropriate receptors), where they would be most efficacious. Another aspect of this problem is the necessity to administer a relatively large amount of an expensive drug, in order that a very small fraction will reach the appropriate body site and exert a pharmacological effect. The usual procedures for drug administration are consequently uneconomical and also frequently produce undesired side-effects.

It is an important object of the present invention to advance the science of pharmacology in order to avoid so far as possible the problems set forth in the preceding paragraph. Other objects of the invention will appear from the description which follows.

SUMMARY OF THE INVENTION

In one aspect, the present invention provides an acylate which is the reaction product of: (a) a substance which is selected from the group consisting of naturally occurring α-aminocarboxylic acids, neurotransmitters other than such acids, and central nervous system pharmacologically active compounds, and containing a functional group including an acylatable hydrogen atom, or a reactive derivative thereof; and (b) an essential fatty acid or a reactive derivative thereof.

In another aspect, the invention provides use of at least one acylate as defined in the preceding paragraph, in the manufacture of a medicament for treatment of a disease or condition related to a neurotransmitter defect or deficiency, or to another central or peripheral nervous system defect or deficiency.

In still another aspect, the invention provides a method for treatment of a disease or condition related to a neurotransmitter defect or deficiency, or to another central or peripheral nervous system defect or deficiency, wherein there is administered to a human or non-human mammal an effective amount of at least one acylate as defined in the last paragraph but one.

In yet a further aspect, the present invention also provides a pharmaceutical formulation which comprises at least one acylate of the invention, together with at least one carrier, diluent or adjuvant.

For the avoidance of doubt, it is to be noted that the preparation of the acylates of the present invention involves the formation of a covalent bond or bonds between a substance defined under (a), above, and one or more molecular proportions of component (b) as defined above. The acylates may be N-acylates, O-acylates or S-acylates, or a mixture of more than one of these types of acylate.

Included in the compounds of the present invention are functional derivatives of the present acylates, and in particular of such acylates which contain residual amino, carboxyl and/or hydroxyl groups. The nature and range of such functional groups will be well known to persons of the art. Presently preferred functional derivatives of acylates containing one or more carboxylic groups are esters thereof with alcohols containing 1–4 carbon atoms. The functional derivatives appear to have similar biological activity to the non-functionalized acylates.

While the scope of the present invention is deemed not to be restricted by any theory, it is nevertheless presently believed that enzymes associated with relevant receptors will split the covalent bond between moieties (a) and (b), whereby component (a) exhibits its pharmacological activity at the site in question while the essential fatty acid—component (b)—is absorbed in the neuronal membrane.

DETAILED DESCRIPTION OF THE INVENTION

The acylates of the present invention, which by way of non-limiting exemplification may result from acylation with formation of a —CO—O—, —CO—S— or —CO—NR$^1$R$^2$ moiety (where each of R$^1$ and R$^2$ is independently selected from a hydrogen atom or an optionally substituted hydrocarbyl group and NR$^1$R$^2$ may also constitute a heterocyclic ring), may be prepared by any of the appropriate methods known to the organic chemist, and thus the manner of their preparation does not constitute, per se, a part of the present invention. Where, in the standard methods of reaction for preparing e.g., the amides, esters or thioesters which may be acylates according to the present invention, reactant (a) contains an atom or substituent which interferes with such reaction, then such interfering atom or substituent may be blocked or protected in a manner known to persons in the art.

Although the present acylates will frequently be prodrugs, that is, substances which when administered in the animal or human body release at the desired site a pharmacologically active entity, nevertheless, this in the alternative or additionally, the acylates may have pharmacological activity in their own right. Further, the acylates include substances in which component (a) is not itself pharmacologically active at the target site, but when released metabolizes to a substance having desired pharmacological activity.

Group (a) substances include naturally occurring (x-aminocarboxylic acids, which are of course "building blocks" in the formation of proteins which perform important functions in the animal and human body, and at least some of which acids functional also as neurotransmitters. Exemplary amino acids are α-aminocarboxylic acids and are selected from alanine, arginine, asparagine, aspartic acid, β-carboxyaspartic acid, γ-carboxyglutamic acid, cysteine, cystine, glutamine, glutamic acid, glycine, histidine, homoserine, hydroxylysine, hydroxyproline, isoleucine, leucine, lysine, methionine, phenylalanine, proline, serine, threonine, tryptophan, tyrosine and valine.

Two amino acids of particular importance, tyrosine and tryptophan, are not formed in the body but must be ingested in food. Tyrosine is metabolized successively to dopa, dopamine, norepinephrine and epinephrine (Scheme A, below), while tryptophan is metabolized first to 5-hydroxytryptophan and thus to 5-hydroxytryptamine (Scheme B, below).

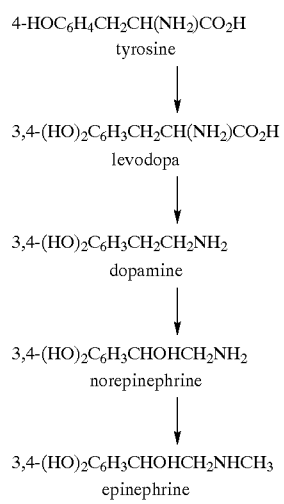

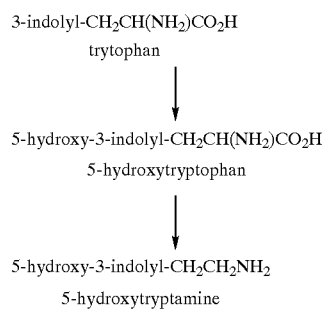

Group (a) substances further include other neurotransmitters, e.g., γ-aminobutyric acid (GABA), Dopamine, Epinephrine, Norepinephrine and 5-hydroxytryptamine. It will be apparent that the amino acids tyrosine and tryptophan thus perform, in the present context, the invaluable function of forming neurotransmitters in the body.

While Parkinson's Disease is related to a deficiency of the central neurotransmitter dopamine, this cannot be administered to patients because is cannot pass the blood-brain barrier. The conventional solution to this problem is the administration of Levodopa; however, this always causes undesirable side-effects, to a greater or lesser extent. Thus, in accordance with an embodiment of the present invention, there is provided a method for the treatment of Parkinson's Disease which comprises treating a patient with an effective amount of at least one compound selected from N- and/or O-acylated derivatives of tyrosine, levodopa and dopamine, where the acyl group is that of an essential fatty acid, such as, e.g., α- or γ-linolenoyl, linoleoyl or arachidonoyl.

Such derivatives constitute presently preferred acylates of the invention, as do also the N- and/or O-acylated derivatives of epinephrine and norepinephrine; the N-acylated derivatives of tryptophan; and the N- and/or O-acylated derivatives of 5-hydroxytryptophan and 5-hydroxytryptamine, in all of which the acyl group is that of an essential fatty acid, such as, e.g., α- or γ-linolenoyl, linoleoyl or arachidonoyl.

It is believed to be a clear implication from the specific example set forth herein, that the acylates of the present invention (in relation to central neurotransmitters and the treatment of CNS-related conditions generally) are able to pass the blood-brain barrier, and it may be predicted with a reasonable degree of confidence that they would have the ability also to access appropriate receptors in relation to peripheral nervous system conditions.

By definition, substance (a) must contain a functional group including an acylatable hydrogen atom, or a reactive derivative thereof, in order that it may potentially be reacted with an essential fatty acid (or a reactive derivative thereof), so as to result in formation of a prodrug according to the present invention. The Table which follows shows, by way of non-limiting illustration only, substances (a), classified according to their pharmacological activity, and indicating the nature of the functional group (rather than the category of compound) containing the hydrogen atom substitutable by e.g., α- or γ-linolenoyl, linoleoyl or arachidonoyl.

TABLE 1

| pharmacological activity | substance | functional group(s) |
|---|---|---|
| cholinomimetic | Metoclopramide | aromatic $NH_2$ |
| anticholinesterase | Edrophonium | aromatic OH |
| antimuscarinic | Cyclopentolate | tertiary OH |
|  | Tropicamide | primary OH |
| sympathomimetic | Epinephrine | {phenolic + sec. OH {(aliphatic) $NHCH_3$ |
|  | Dopamine | {phenolic OH {(aliphatic)$NH_2$ |
| α-adrenergic blocker | Phentolamine | {phenolic OH {ring NH |
| β-adrenergic blocker | Propranolol | {secondary OH {(aliphatic)NHisoPr |
| adrenergic inhibitor | Guanethidine | amidine |
| ganglionic stimulator | Lobeline | secondary OH |
| ganglionic blocker | Mecamylamine | secondary OH |
| neuromuscular blocker | d-Tubocurarine | phenolic OH |
| general anesthetic | Lorazepam | {secondary OH {ring NH |
| local anesthetic | Procaine | aromatic $NH_2$ |
| hypnotic } antiepileptic } | Nitrazepam | ring NH |
| sedative-hypnotic | Ethchlorvynol | tertiary OH |
| psychiatric | Haloperidol | tertiary OH |
|  | Desipramine | aliphatic NH |
| anti-Parkinson | Levodopa | {phenolic OH {(aliphatic)$NH_2$ |
| anti-spastic | Baclofen | (aliphatic)$NH_2$ |
| opioid analgesic | Morphine | {phenolic + sec. OH |
| opioid antagonist | Naloxone | phenolic OH |
| CNS stimulant | Methylphenidate | ring NH |
| neurotransmitter | α-aminocarboxylic acids* γ-aminobutyric acid (GABA) } Dopamine (see above) Epinephrine (see above) Norepinephrine | }(aliphatic) $NH_2$ {phenolic + sec. OH {(aliphatic) $NH_2$ |
|  | 5-hydroxytryptamine (seratonine) | {phenolic OH {(aliphatic) $NH_2$ |

*α-aminocarboxylic acids may contain also OH or SH functions, which may be acylated additionally or alternatively The acylates of the invention may be formulated with carriers, diluents and adjuvants as is well known in the pharmaceutical art and they may be administered in the usual modes, such as orally, parenterally, rectally of transdermally. Consequently, the present pharmaceutical formulations, except insofar as they contain the present novel and inventive acylates, are not otherwise to be regarded as innovative per se, and they may be manufactured and administered by known methods.

The invention will now be illustrated by the following Examples.

EXAMPLE 1

N-α-linolenyltyrosine

Similarly to the method described by Inman, J. K. et al., Enzyme Structure, 1983, vol. 91 p. 564, Academic Press, acetonitrile (0.25 ml) and methanol (1 ml) were dissolved in ether (5 ml). In presence of anhydrous calcium sulfate, and in a nitrogen atmosphere, the solution, kept at 0° C., was saturated with anhydrous HCI, and thereafter maintained at 0° C. for two hours. The solution was shaken with dry ether (50 ml) and after standing a further hour at 0° C., the product crystallized out and was collected by decantation and washing with 2–10 ml cold dry ether. It was dried under vacuum and stored for 24 hours prior to use in a tightly stoppered bottle under anhydrous conditions at −20° C.

The initially formed methylacetamidate hydrochloride was reacted in known manner with tyrosine (1 g) and α-linolenic acid (1 ml), and the desired N-(α-linolenoyl) tyrosine was isolated. The identity of the product as N-(α-linolenoyl)tyrosine was confirmed by testing in a mass spectrometer (VG70) which showed the presence of N-(α-linolenoyl) and tyrosine moieties, as well as by use of a plane-polarized infrared spectrophotometer (Varian IR 427) which inter alia showed the presence of the amide group.

In an alternative method, the carboxylic acid function in tyrosine is protected prior to reaction with α-linolenic acid (or a reactive derivative thereof), and the resultant carboxyl-protected N-(α-linolenoyl)tyrosine is deprotected, giving the desired product.

BIOLOGICAL TESTING OF N-β-LINOLENYLTYROSINE (I)

Rotational Behavior

One of the major behavioral methods to measure the increase in dopamine activity in the brain is rotational behavior. Dopamine is the neurotransmitter in the striatum. The striatum controls motor movements and motor integration. In the brain there are two striata, in the right and left hemispheres, respectively. Unilateral ablation of a striatum will result in walking in circles, as the intact striatum is still functioning; Ungerstadt, U. et al., Brain Res., 1970, 24: 485–492, created a lesion in one striatum and measured the effect on rotational behavior. Since then, this technique has been used to screen molecules, such as stimulants or potential anti-Parkinson drugs, which induce increase in dopaminergic activity.

Experimental Animals

Groups of 6 male Sprague-Dawley rats (Charles River Laboratories, Wilmington, Mass.) weighing 100–120 g, were housed 6 per cage in a well-ventilated and air-conditioned room of ambient temperature (22±2° C.) and relative humidity 45%. The rats had access to food (Big Red Laboratory Chow, Agway Inc., Syracuse, N.Y.) and water ad libitum. Light ("Vita Light", Duro Test Corp., North Bergen, N.J.) was provided between 9 am and 9 pm.

Lesions

All surgery was performed under anesthesia (sodium pentobarbital, 50 mg/ml, as required). The rats were placed in a Kopf stereotaxic instrument (model #900). Unilateral anodal electrolytic lesions were made with constant current supply (lesion-producing device #58040, Stoelting, Chicago, Ill.). Current (2.0 mV for 10 seconds) was passed through stainless steel insulated wire pe 32, 0.008 inches diameter ("Formax", Stoelting, Chicago, Ill.), bared only at the tip. The coordinates (modified from Konig and Klippel, 1963) for caudate nucleus lesion were: A 8.5, L 2.2, V+1.8. The lesions were made in the left side of the brain. Tests were made at day 4 after surgery.

Rotational Behavior

Rotational behavior was tested in a rotameter, modified from the design of Ungerstedt et al., 1970. Each rat, mounted in a special harness, was placed in an acrylic transparent dome of 41 cm radius. Its rotational movements were transduced from the harness via a stainless steel tube (⅛ inch) and a precision universal joint (Pic BC 12) to a 5K linear potentiometer (Spoctrol), which received an excitation current from a Sanborn Polygraph (7702 B recorder, Hewlett-Packard). The potentiometer (preamplifier 8805 A) measured and recorded the changes in the amount of current which passed through it, resulting from the rotational movements of the rats. When each rat turned to the right, the recording pen was deflected upward; a leftward turn deflected the pen downward. Continuous recordings were made on chart paper RJN at a speed of 1 mm/sec.

Procedure

Each rat was placed in the rotameter and treated with an i.p. injection of saline or (I) (10 mg/kg) as prepared above. Two observers watched the rats for abnormal behavior (i.e. stereotype—which was not found). The frequency of turning was measured between 30–40 minutes post-injection. After this time lapse, the treated rats had increased their rate of rotational motion from 4 cycles/minute to 40 cycles/minute.

At the end of the experiment, the rats were removed from the rotameter and the brain was taken for verification of the lesion as follows. The rats were given an overdose of pentobarbital and perfused with saline, followed by 10% formalin. Brains were removed and serial coronal slices were made at 40 microns using a freezing microtome. Representative slices were stained with Cresyl Violet and mounted on slides. The histological examination showed that in all tested rats the lesion was confined to the striatum. All other brain areas were intact.

EXAMPLE 2

N-β-linolenyltyrosine Methyl Ester

This functional derivative of N-β-linolenyltyrosine was prepared as follows. To an ice-cooled solution of p-tert-butoxy-β-phenylalanine methyl ester, HCl salt (2.1 g) in $CH_2Cl_2$ (50 ml), in an argon atmosphere, was added dropwise $Et_3N$ (1 ml=0.74 g), and then—after three minutes-β-linolenic acid (1.8 g) in $CH_2Cl_2$ (35 ml), followed by (as solids) dicyclohexylcarbodiimide (1.5 g) and hydroxybenzotriazole (0.96 g), and then DMF (35 ml), the temperature being maintained at 0° C. for two hours, with stirring, and finally at room temperature for 40 hours. Ethyl acetate (50 ml) was added, and the mixture was filtered, concentrated in vacuo, and again filtered. Ether (30 ml was added and the mixture was extracted successively with water, 1% aq. HCl, 1% aq. KOH and water. The organic phase was dried ($MgSO_4$) and after filtration and evaporation, a mixture of trifluoroacetic acid (70 ml) and triethylsilane (1 ml) were added to the residue at −10° C. (argon atmosphere). The mixture was stirred for 20 minutes at 0° C., after which it was allowed to attain ambient temperature, stirred for 5 minutes, evaporated in vacuo at 30° C., re-evaporated with methanol (4×50 ml), and finally chromatographed on a Merck silica column (h=30 cm, d=3.2 cm). Elution was effected with $CHCl_3$ (1.5 l), UV detection at 270 nm, the product being obtained as a viscous oil (2 g), elemental composition confirmed by mass spectrum as $C_{28}H_{41}NO_4$.

High resolution mass-spectrum (Cl by $CH_4$): 456.310112 (M+, 100%), $C_{28}H_{42}NO_4$ calc. 456.311384. $^1H$—NMR ($CDCL_3$): 0.97 (t, J=7.5 Hz; 3H), 1.28 (broadened; 10H), 1.58 (m; 2H), 2.07 (m; 4H), 2.19 (t, J=5.6 Hz; 2H), 2.80 (m; 2H), 3.03 (m; 2H), 3.37 (s; 3H), 4.87 (m; 1H), 5.37 (m; 6H), 6.04 (d, J=8.0 Hz; 1H), 6.10 (broadened; 1H), 6.83 (m, 4H) ppm. $^{13}C$—NMR ($CDCl_3$): 14.24; 20.51; 25.49; 25.52; 25.57; 27.16; 29.08; 29.15; 29.54; 36.48; 37.18; 52.40; 53.17; 115.53;126.94; 127.07; 127.70; 128.21; 128.27; 130.21; 131.93; 155.45; 172.30; 173.53 ppm.

BIOLOGICAL TESTING OF N-α-LINOLENYLTYROSINE. METHYL ESTER (II)

Experimental Animals

Three groups of 12 male Sprague-Dawley rats (Charles River Laboratories, Wilmington, Mass.) weighing 100–150 g, were housed 6 per cage in a well-ventilated and air-conditioned room of ambient temperature (22±2° C.) and relative humidity 45%. The rats had access to food (Big Red Laboratory Chow, Agway Inc., Syracuse, N.Y.) and water ad libitum. Light ("Vita Light", Duro Test Corp., North Bergen, N.J.) was provided between 9 am and 9 pm. These groups were used for rotational study, the dosage of (II) being 100 mg/kg, i.p.

Rotational Behavior

1. Lesions

One group served as a control group (no treatment), a second group was a sham operated group, and a third group was the operated group. All surgery was performed under anesthesia (sodium pentobarbital, 50 mg/ml, as required). The rats were placed in a Kopf stereotaxic instrument (model #900). Unilateral anodal electrolytic lesions were made with constant current supply (lesion-producing device #58040, Stoelting, Chicago, Ill.). Current (2.0 mV for 10 seconds) was passed through stainless steel insulated wire pc 32, 0.008 inches diameter ("Formax", Stoelting, Chicago, Ill.), bared only at the tip. The coordinates (modified from Konig and Klippel, 1963) for caudate nucleus lesion were: A 8.5, L 2.2, V+1.8. The lesions were made in the left side of the brain. Sham operated animals were treated as lesioned animals, i.e. they were placed in the stereotaxic instrument and an electrode was placed in the brain, but without passing electric current therethrough. After surgery, each rat was placed in an individual cage. Tests were made at day 10 after surgery. At the end of the experiment, each rat was given an overdose of pentobarbital and perfused with saline, followed by 10% formalin. Brains were removed and serial coronal slices were made at 40 micra, using a freezing microtome. Representative slides were stained with Cresyl Violet for verification of the lesion.

2. Procedure

Details of the procedure with regard to determination of rotational behavior were substantially as described above for testing (I).

3. Results

Results are summarized in the following Table, which demonstrates that administration of (II) influences rotational behavior in a statistically significant manner (ANOVA $p \leq 0.001$).

| Group | No. of rats in group | L | R | L + R | % L | % R |
| --- | --- | --- | --- | --- | --- | --- |
| Control + vehicle | 10 | 12 | 8 | 20 | 60 | 40 |
| sham + vehicle | 12 | 7 | 21 | 28 | 25 | 75 |
| lesion + vehicle | 11 | 3 | 27 | 30 | 10 | 90 |
| lesion + (II) | 11 | 98 | 2 | 100 | 98 | 2 |

Blephrospasm

This is an involuntary spasm of the orbicular muscles of the eye, causing forceful closure of the eyes. Symptomatically there is a significant increase in the rate of eyelid closures/min. This phenomenon is regarded as a type of dystonia, a decrease in the brain dopamine level being the etiology of this syndrome. Ro4-1284 is a powerful dopamine-depleting agent. In saline-treated animals, Ro4-1284 is able to induce an animal model of benign essential blephrospasm. Groups of rats similar to those described above were treated daily for 14 days with 25 mg/kg (II), i.p., and then were challenged with a dose of 40 mg/kg Ro4-1284, i.p. The results of this test were shown in the following Table.

| Group | No. of rats in group | rate of eyelid blinking/min.* |
|---|---|---|
| Control | 12 | $5.16 \pm 1.58$ |
| Ro4-1284 | 12 | $19.08 \pm 3.4$ |
| (II) followed | 12 | $5.00 \pm 1.95$ |
| by Ro4-1284 | | ($p < 0.001$) |

*30 minutes after treatment with Ro4-1284

Conclusions of Biological testing (I) and (II) cross the blood-brain barrier and are enzymatically converted to one or more of dopamine, norepinephrine and epinephrine. To the best of the inventor's knowledge, it has never been recorded that either α-linolenic acid or tyrosine influence rotational motion or blephrospasm as was found in these experiments. By implication, the acylates of the present invention generally, including their functional derivatives, should be capable of crossing the blood-brain barrier and/or accessing the relevant receptors.

While the present invention has been particularly described with reference to certain embodiments, it will be apparent to those skilled in the art that many modifications and variations may be made. The invention is accordingly not to be construed as limited in any way by such embodiments, rather its concept is to be understood according to the spirit and scope of the claims which follow.

What is claimed is:

1. Method for treatment of a disease or condition related to a neurotransmitter defect or deficiency, or to another central or peripheral nervous sysem defect or deficiency, wherein there is administered to a human or non-human mammal an effective amount of at least one acylate which is the reaction product of (a) a substance which is selected from the group consisting of naturally occurring α-aminocarboxylic acids, neurotransmitters other than such acids, and central or peripheral nervous system pharmacologically active compounds, and containing a functional group including an acylatable hydrogen atom, or a reactive derivative thereof; and (b) an essential fatty acid or a reactive derivative thereof, and including the pharmaceutically acceptable salts of such acylates possessing a basic and(or) acidic function, or of a functional derivative of said acylate including the pharmaceutically acceptable salts of such functional derivative possessing a basic and(or) acidic function; provided that component (b) excludes Δ-4,7,10,13,16,19-docosahexaenoic acid or a reactive derivative thereof.

2. Method according to claim 1, for the treatment of Parkinson's Disease, which comprises treating a patient with an effective amount of at least one compound selected from N- and/or O-acylated derivatives of tyrosine, levodopa and dopamine, where the acyl group is α- or γ-linolenoyl, linoleoyl or arachidonoyl.

3. Method according to claim 1, wherein said reaction resulted in the formation of a —CO—O— moiety; a —CO—S— moiety; or a moiety of formula —CO—NR$^1$R$^2$ where each of R$^1$ and R$^2$ is independently selected from a hydrogen atom or an optionally substituted hydrocarbyl group and NR$^1$R$^2$ may also constitute a heterocyclic ring.

4. Method according to claim 1, wherein said pharmacologically active compounds are selected from among cholinomimetics, anticholinesterase agents, antimuscarinic drugs, sympathomimetic amines, adrenergic blockers and inhibitors, ganglionic stimulators and blockers, neuromuscular blockers, general and local anesthetics, hypnotics, sedatives, psychiatric drugs, antiepileptics, anti-Parkinsonism drugs, anti-spasticity drugs, opioid analgesics and antagonists and central nervous system stimulants.

5. Method according to claim 1, wherein said naturally occurring α-aminocarboxylic acids are selected from alanine, arginine, asparagine, aspartic acid, β-carboxyaspartic acid, γ-carboxyglutamic acid, cysteine, cystine, glutamine, glutamic acid, glycine, histidine, homoserine, hydroxylysine, hydroxyproline, isoleucine, leucine, lysine, methionine, phenylalanine, proline, serine, threonine, tryptophan, tyrosine and valine.

6. Method according to claim 1, wherein said other neurotransmitters are selected from γ-aminobutyric acid (GABA), dopamine, epinephrine, norepinephrine and 5-hydroxytryptamine.

7. Method according to claim 1, wherein said at least one acylate comprises an N-acylated drivative of tryptophan; or an N- and/or O-acylated derivative of tyrosine, where the acyl group is α- or γ-linolenoyl, linoleoyl or arachidonoyl.

8. Method according to claim 1, wherein said at least one acylate comprises an N- and/or O-acylated derivative of dopamine, epinephrine, norepinephrine or 5-hydroxytryptamine, where the acyl group is α- or γ-linolenoyl, linoleoyl or arachidonoyl.

9. Method according to claim 1, wherein said at least one acylate comprises an N- and/or O-acylated derivative of levodopa or 5-hydroxytryptophan, where the acyl group is α- or γ-linolenoyl, linoleoyl or arachidonoyl.

10. An acylate which is the reaction produce of (a) a substance which is selected from the group consisting of neurotransmitters other than naturally occurring α-aminocarboxylic acids, and central or peripheral nervous system pharmacologically active compounds, and containing a functional group including an acylatable hydrogen atom, or a reactive derivative thereof, and (b) an essential fatty acid or a reactive derivative thereof; and including the pharmaceutically acceptable salts of such acylates possessing a basic and(or) acidic function; and a functional derivative of said acylate including the pharmaceutically acceptable salts of such functional derivative possessing a basic and(or) acidic function;

provided that component (b) excludes Δ-4, 7, 10, 13, 16, 19-docosahexaenoic acid or a reactive derivative thereof, and that component (a) is not dopamine or a reactive derivative thereof, when simultaneously component (b) is either linoleic acid or a reactive derivative thereof or is linolenic acid or a reactive derivative thereof.

11. Acylate according to claim 1, wherein said reaction results in the formation of a —CO—O— moiety; a —CO—S— moiety; or a moiety of formula —CO—NR$^1$R$^2$, where each of R$^1$ and R$^2$ is independently selected from a hydrogen atom or an optionally substituted hydrocarbyl group and NR$^1$R$_2$ may also constitute a heterocyclic ring.

12. Acylate according to claim 10, wherein said pharmacologically active compounds are selected from among cholinomimetics, anticholinesterase agents, antimuscarinic drugs, sympathomimetic amines, adrenergic blockers and inhibitors, ganglionic stimulators and blockers, neuromuscular blockers; general and local anesthetics, hypnotics, sedatives, psychiatric drugs, antiepileptics, anti-Parkinsonism drugs, anti-spasticity drugs, opioid analgesics and antagonists and central nervous system stimulants.

13. Acylate according to claim 10, wherein said other neurotransmitters are selected from γ-aminobutyric acid (GABA), dopamine, epinephrine, norepinephrine and 5-hydorxytryptamine.

14. Acylate according to claim 10, which is an N-acylated derivative of tryptophan; or an N- and/or O-acylated derivative of tyrosine, where the acyl group is α- or γ-linolenoyl, linoleoyl or arachidonoyl.

15. Acylate according to claim 10, which is an N- and/or O-acylated derivative of dopamine, epinephrine, norepinephrine or 5-hydroxytryptamine, where the acyl group is α- or γ-linolenoyl, linoleoyl or arachidonoyl.

16. Acylate according to claim 10, which is an N- and/or O-acylated derivative of levodopa or 5-hydroxytryptophan, where the acyl group is α- or γ-linolenoyl, linoleoyl or arachidonoyl.

17. A pharmaceutical formulation which comprises at least one acylate as defined in claim 10, together with at least one carrier, diluent or adjuvant.

* * * * *